(12) United States Patent
Steinboeck et al.

(10) Patent No.: US 9,075,033 B2
(45) Date of Patent: Jul. 7, 2015

(54) REAGENT CARTRIDGE

(75) Inventors: Wolf-Dietrich Steinboeck, Graz (AT); Wolfgang Hofmann, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 39 days.

(21) Appl. No.: 12/349,685

(22) Filed: Jan. 7, 2009

(65) Prior Publication Data

US 2009/0176314 A1    Jul. 9, 2009

(30) Foreign Application Priority Data

Jan. 7, 2008  (EP) .................................... 08100167

(51) Int. Cl.
| | | |
|---|---|---|
| G01N 1/00 | (2006.01) | |
| B01L 3/00 | (2006.01) | |
| G01N 35/00 | (2006.01) | |
| G01N 35/10 | (2006.01) | |

(52) U.S. Cl.
CPC ........... G01N 35/1002 (2013.01); *Y10T 436/25* (2015.01); B01L 3/502 (2013.01); *B01L 2200/16* (2013.01); *B01L 2300/0663* (2013.01); *B01L 2300/0816* (2013.01); *B01L 2300/0867* (2013.01); *B01L 2400/0487* (2013.01); *B01L 2400/0644* (2013.01)

(58) Field of Classification Search
CPC ................. B01L 3/502; B01L 2200/16; B01L 2300/0663; B01L 2300/0816; B01L 2300/0867; B01L 2400/0487; B01L 2400/0644; G01N 35/1002; Y10T 436/25
See application file for complete search history.

(56) References Cited

U.S. PATENT DOCUMENTS

| | | | | |
|---|---|---|---|---|
| 2,938,351 | A | * | 5/1960 | Brooks ........................... 91/515 |
| 3,929,413 | A | | 12/1975 | Young et al. |
| 4,499,053 | A | | 2/1985 | Jones |
| 5,140,845 | A | * | 8/1992 | Robbins ...................... 73/19.03 |
| 5,279,797 | A | * | 1/1994 | Burns et al. ................... 422/555 |
| 5,422,079 | A | | 6/1995 | Parekh et al. |

(Continued)

FOREIGN PATENT DOCUMENTS

| | | |
|---|---|---|
| DE | 3502546 A1 | 8/1985 |
| EP | 1 495 809 A | 1/2005 |

(Continued)

OTHER PUBLICATIONS

Brouwer, H. "Inexpensive reagent dispenser." Journal of Chemical Education (1994) 71 p. A148.*

(Continued)

*Primary Examiner* — Christopher A Hixson
(74) *Attorney, Agent, or Firm* — Dinsmore & Shohl LLP

(57) ABSTRACT

A reagent cartridge which can be exchangeably inserted into an analyzer and having a plurality of reagent bags furnished with connecting lines, each of which may optionally be connected to an input device of the analyzer, and method for operating the analyzer are disclosed. Each reagent bag has an analyzer-controlled multi-way valve with at least two valve positions at the point where the respective connecting line departs, such that the first valve position opens a fluid path between the connecting line and the reagent bag, while the second valve position closes off the reagent bag and opens a fluid path between a ventilation source, e.g. ambient air, and the connecting line. The connecting lines of the reagent bags departing from the multi-way valve open directly into a common rail or a collector valve.

12 Claims, 3 Drawing Sheets

(56) References Cited

U.S. PATENT DOCUMENTS

| | | | |
|---|---|---|---|
| 5,665,315 A | 9/1997 | Robert et al. | |
| 5,780,302 A | 7/1998 | Conlon et al. | |
| 5,882,602 A | 3/1999 | Savage et al. | |
| 5,885,533 A * | 3/1999 | Savage et al. | 422/555 |
| 6,872,297 B2 | 3/2005 | Mansouri et al. | |
| 2003/0000833 A1* | 1/2003 | Mansouri et al. | 204/402 |
| 2004/0047771 A1 | 3/2004 | Conlon et al. | |
| 2005/0008505 A1 | 1/2005 | Lapp et al. | |

FOREIGN PATENT DOCUMENTS

| | | |
|---|---|---|
| JP | 60-176174 U | 11/1985 |
| WO | WO 2006048678 A2 * | 5/2006 |

OTHER PUBLICATIONS

Gaensler, Edward A. et al. "Attachment for automated single breath diffusing capacity measurement." Chest (1973) 63 136-145.*
Robbins et al. "A field screeing system for gasoline contamination using a polyethylene bag sampling system." GWMR 1999 pp. 87-97.*
Economou, A., "Sequential-injection analysis (SIA): A useful tool for on-line sample-handling and pre-treatment", Trends in Analytical Chemistry, vol. 24, No. 5, 2005, pp. 416-425.
Fang, Zhao-Lun, "Contiuous monitoring in drug dissolution testing using flow injection systems", Trends in Analytical Chemistry, vol. 18, No. 4, 1999, pp. 261-271.
European Search Report, dated Apr. 24, 2008.

* cited by examiner

Fig. 5
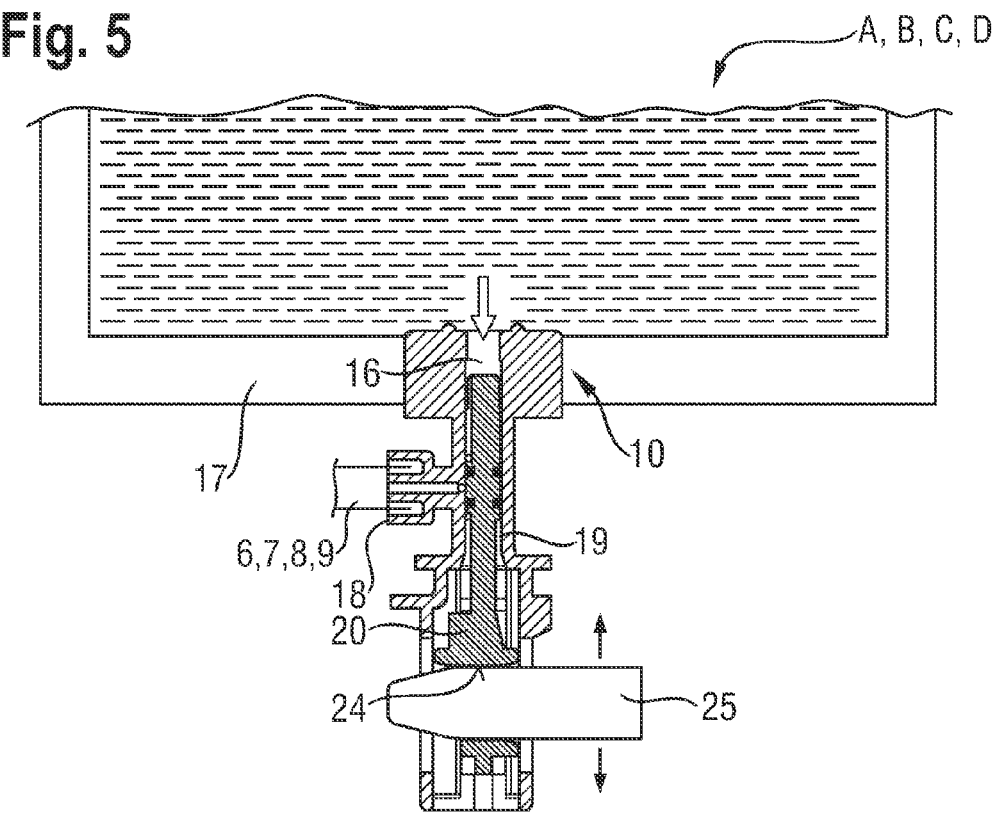
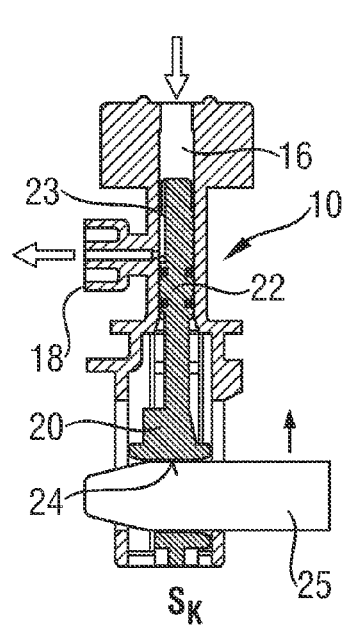
Fig. 6
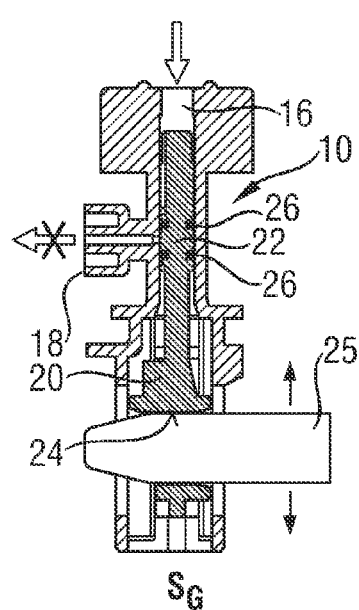
Fig. 7
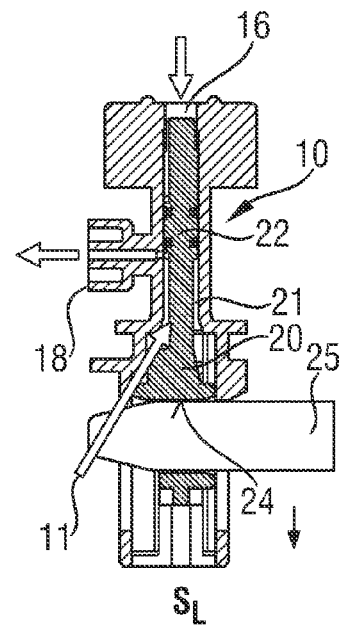
Fig. 8

REAGENT CARTRIDGE

CROSS REFERENCE TO RELATED APPLICATIONS

This application claims priority to EP 08100167.9, filed on 7 Jan. 2008, the disclosure of which is herein fully incorporated by reference.

FIELD OF THE INVENTION

Embodiments of the invention relate generally to reagent cartridges and analyzers which use reagent cartridges, and in particular to a reagent cartridge, which can be exchangeably inserted into an analyzer and comprises a plurality of reagent bags furnished with connecting lines, each of which may optionally be connected to an input device of the analyzer and which include a valve located in the connecting line, and a method for operating an analyzer which is provided with a measuring chamber and an exchangeable reagent cartridge.

BACKGROUND OF THE INVENTION

Analyzers are used for decentralized determination of a number of parameters in whole blood. Such an analyzer may be, for instance, a portable analyzer for determining POC (Point of Care) parameters, i.e. blood gases ($O_2$, $CO_2$, pH), electrolytes ($K^+$, $Na^+$, $Ca^{++}$, $Cl^-$), metabolites (glucose and lactate), haematocrit, haemoglobin parameters (tHb, $SO_2$, etc.) and bilirubin. Although such known analyzers are suitable for their intended purposes, further improvements are desired to address inherent deficiencies which detract from their utility.

For example, one problem to be solved concerns a way of connecting a plurality of reagent bags to the analyzer, such that all fluids, i.e. the sample (e.g. blood), which may be taken from diverse sample containers, external quality control (QC) fluids, and functional fluids present in the reagent bags of the reagent cartridge, such as calibrating, QC, rinsing, disinfecting and cleansing fluids, enter into the analyzer via a single input element (e.g. an input needle).

The partly tonometered functional fluids are contained in reagent bags (e.g. heat-sealed laminated aluminium bags). In known applications the reagent bags are closed prior to use in the analyzer with a septum or a valve (bag valve), which is irreversibly opened when the bag is inserted into the analyzer, releasing the bag's content.

It must be ensured that no cross-contamination of the sample content to be measured, or of calibrating and QC-fluids will occur. Furthermore it must be guaranteed that the composition of the gas mixture contained in the tonometered fluids of the bags or tubes will remain constant during operation but also during longer standby phases.

In this context there is known from DE 35 02 546 C2 an analyzer for measuring liquid and gaseous samples, in which the input element (e.g. a hollow needle) of the sample input assembly in its initial position seals the analyzer path against a docking element, which connects to tubes for the feeding of calibrating and standard media and to a valve-controlled air inlet. If the input element is tilted out of its initial position sample fluids from diverse sample containers can be entered. By providing air entry via a valve for separating the individual fluid samples or for drying of the sample path no other valves or shut-off devices are required. The shut-off valves of the individual reagent containers, which are separately exchangeable, are designed as simple blocking valves. U.S. Pat. No. 4,499,053 A discloses a similar type of analyzer.

It is disadvantageous that the lines from the reagent containers up to the shut-off valves and onwards from the shut-off valves to the fittings in the feeder line of the docking element cannot be emptied, or rather that these lines cannot be emptied without the fluid contained in the lines running back into the reagent containers and introducing air into the containers, thus changing the gas concentrations of the tonometered calibrating fluids.

Instead of the rigid reagent containers formerly used, flexible, heat-sealed bags made of laminated foil (e.g. aluminium foil) are preferred now.

The use of reagent bags contained in exchangeable reagent cartridges in blood analyzers has frequently been described in the patent literature, for example in U.S. Pat. No. 5,882,602A, U.S. Pat. No. 5,780,302 A and U.S. Pat. No. 6,872,297 B2.

U.S. Pat. No. 5,882,602 A for instance discloses a self-sealing valve in combination with a "flow fitting". This means a septum made of an elastomer in the connecting element of the reagent bag, which on insertion into the analyzer is punctured by a needle. A bag connection described in U.S. Pat. No. 5,780,302 A is of similar kind.

The embodiment as shown in FIG. 1 of U.S. Pat. No. 6,872,297 B2 has an exchangeable reagent cartridge (disposable cartridge) with a plurality of reagent bags with calibrating and rinsing fluids (A, B, Rinse) whose connecting lines are led via a rotary valve and a "common rail" to the tiltable cannula of an input unit. From there the fluids are fed via another line into the measuring chamber and finally via a peristaltic pump into a waste container, which is also contained in the reagent cartridge. In a certain position of the rotary valve air can be fed into the common rail.

In the variant with a rotary valve of U.S. Pat. No. 6,872,297 A once again the connecting lines leading from the reagent bags to the rotary valve cannot be emptied without risking contamination of the bag content with air.

While it is known in the art to keep simple open/close valves of the bags closed during shelf storage of the reagent cartridge and to open them for the first time and irreversibly when the cartridge is inserted, the valves will stay open during the period of use of the cartridge and a separate rotary valve will route the fluids through the connecting lines. This arrangement will not permit emptying of the connecting lines. This is a disadvantage especially if the cartridge is used for a longer period of time.

During measurement operation of the analyzer the calibration and quality control fluids contained in the reagent cartridge must be transported contamination-free from the respective reagent bag to the measuring cell via a tube system, a common rail (see for instance DE 35 02 546 C2) or a rotary valve (see for instance U.S. Pat. No. 6,872,297 A) and a hollow needle.

If the apparatus is operational for a prolonged period of time, i.e., taking sample measurements or in standby state (typically between 1 and 8 hours), the gas permeability of the tube material of the individual lines (leading to the common rail or to the rotary valve) will cause significant changes in the gas concentrations of the calibrating or quality control fluids.

SUMMARY OF THE INVENTION

It is against the above background, that embodiments of the present invention provide a reagent cartridge for insertion into an analyzer, which is provided with reagent bags arranged in such a way that gas permeability of a tube material in connecting lines or a back-flow of withdrawn functional fluids will cause no negative effects on gas concentrations of calibrating or quality control fluids.

In one embodiment, a reagent cartridge, which is exchangeably insertable into an analyzer having an input device and a ventilation source, is disclosed. The reagent cartridge comprises a plurality of reagent bags, each of the reagent bags being furnished with a connecting line, each of which is optionally connectable to the input device of the analyzer, wherein each reagent bag has an analyzer-controlled multi-way valve with at least two valve positions at a point where said respective connecting line departs, wherein a first valve position opens a fluid path between the connecting line and the reagent bag, and a second valve position closes off the reagent bag and opens a fluid path between the ventilation source and the connecting line. The second valve position thus avoids back-flow of withdrawn functional fluids from the connecting line, at the same time causing by the admission of air (or an inert gas) the connecting line starting from the bag valve to be dried and sucked free of fluid without contaminating the bag contents with air or inert gas.

In another embodiment, the connecting lines of the reagent bags departing from the multi-way valves open directly into a common rail preceding the input device of the analyzer. By the use of a common rail a valveless connection to the input device of the analyzer may be established, which in combination with the multi-way valves integrated in the individual reagent bags leads to the diverse advantages offered by the invention and described in more detail below.

In an alternative embodiment, the connecting lines departing from the multi-way valves directly lead to a common collector valve preceding the input device, such as for example, a rotary valve in another embodiment.

According to yet another embodiment, each multi-way valve has a third valve position, in which both access to the reagent bag and the fluid path to the ventilation source are closed off. This arrangement ensures that the connecting lines are not contaminated by environmental substances during transport and storage of the reagent cartridges or long pauses between measurements.

In another embodiment, each multi-way valve of the reagent bags is configured as a piston valve, which has a first fitting provided in a peripheral seam of the reagent bag, and a second fitting joined to a connecting line, with a valve piston sliding axially in the valve cylinder of the piston valve, the piston being provided with a sealing region between a first and a second transfer passage, where by shifting the piston each passage or region may be individually aligned with the second fitting.

In one embodiment, each valve piston has an actuating orifice for receiving an actuating element of the analyzer, the actuating elements for the individual bag valves automatically locking into place when the cartridge is inserted in the analyzer.

In another embodiment, disclosed is a reagent bag with a valve placed at the beginning of a connecting line, which has a first valve position which opens a first fluid path between the reagent bag and the connecting line, and a second valve position which opens a second fluid path between a ventilation source and the connecting line. The valve may have a third valve position, in which both the first and second fluid paths are closed.

In still another embodiment, a method for operating an analyzer, which comprises a measuring chamber and an exchangeable reagent cartridge, with reagent bags containing functional fluids, is disclosed. The method comprises drawing a fluid packet from one of the reagent bags by switching a multi-way valve located directly at the reagent bag to a first valve position, such that a fluid path to the contents of the reagent bag is established, and transporting the fluid packet towards the measuring chamber. The method further includes switching the multi-way valve to a second valve position after drawing the fluid packet, such that the path to the contents of the reagent bag is closed and a fluid path to a ventilation source is established, and sucking in the gaseous medium from the ventilation source.

These and other features of various embodiments of the present invention will become apparent from the below detailed discussion and along with the following drawings.

BRIEF DESCRIPTION OF THE DRAWINGS

The invention will now be described in more detail below, with reference to the enclosed drawings, wherein:

FIG. 5 is a diagram showing an embodiment of a reagent cartridge according to the invention with a piston valve heat-sealed into the peripheral seam in a sectional view; and FIGS. 6 to 8 are diagrams showing different valve positions of the piston valve as presented in FIG. 5.

DETAILED DESCRIPTION

Figure 1:
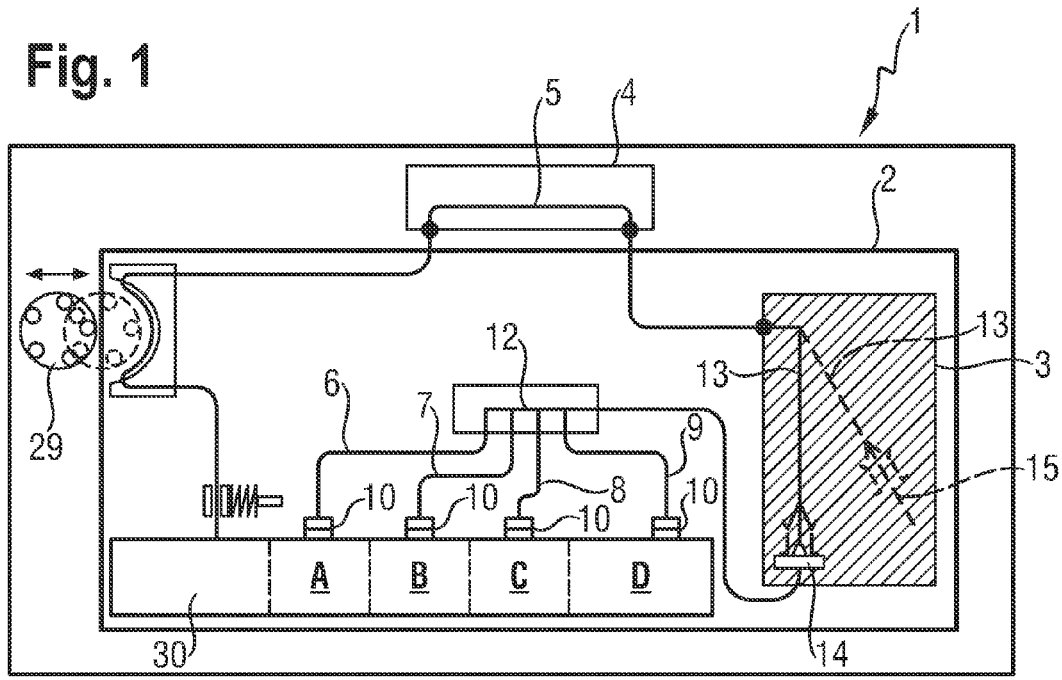
FIG. 1 is a diagram showing an embodiment of a reagent cartridge according to the invention with a plurality of reagent bags with valve controlled connecting lines in schematic representation.

The analyzer 1 schematically shown in FIG. 1 for analyzing medical fluid samples, for instance blood samples, is provided with a reagent cartridge 2, which can exchangeably be inserted into the analyzer 1. The cartridge 2 comprises a plurality of reagent bags A to D, which contain functional fluids such as calibrating means, quality control means, flushing, rinsing and disinfectant solutions, which may be fed individually to an input device 3 and subsequently for instance into a measuring chamber 5 contained in a sensor cartridge 4. The input device 3 of the analyzer 1 is provided with a tiltable input element 13 (for instance a hollow needle), which in a base position connects to a docking element 14 for input of calibrating and rinsing means, and which in a position 15 tilted up from the base position, can take in sample fluids.

In one embodiment, sample input can occur from a variety of containers (e.g. syringe, capillary, glass vessel, etc.) via a movable, for instance tiltable, input element, as is for instance described in DE 35 02 546 C2 or in U.S. Pat. No. 4,499,053 A.

Each reagent bag A to D has at the beginning of the respective connecting line 6, 7, 8, 9 an analyzer-controlled multi-way valve 10 (bag valve) with at least two valve positions, where the first valve position opens a fluid path between the respective connecting line 6, 7, 8, 9 and the corresponding reagent bag A to D. In the second valve position the respective reagent bag A to D is closed, and a fluid path 11 (see FIGS. 2 to 4, for example) between a ventilation source, which in one embodiment is ambient air, and the connecting line 6, 7, 8, 9 is established. All connecting lines 6, 7, 8, 9 of the reagent bags A to D departing from the multi-way valves open directly and without valves into a common rail 12, which connects to the docking element 14 of the sample input device 3. The common rail 12 or the collector part may be made by injection molding. The connecting lines 6 to 9 of the bag valves 10 are for instance made of flexible plastic tubing.

The sample input device 3, with the tiltable input element 13, in one embodiment is an integral part of the reagent cartridge 2 and is replaced together with the cartridge.

The fluid path leads towards the sensor cartridge 4 via the fixed part of a hose pump 29 integrated in the analyzer 1 and ends in a waste bag 30 also contained in the reagent cartridge 2. In the embodiment shown the sensor cartridge 4 is not part of the reagent cartridge 2 and may be exchanged independently.

Figure 2:
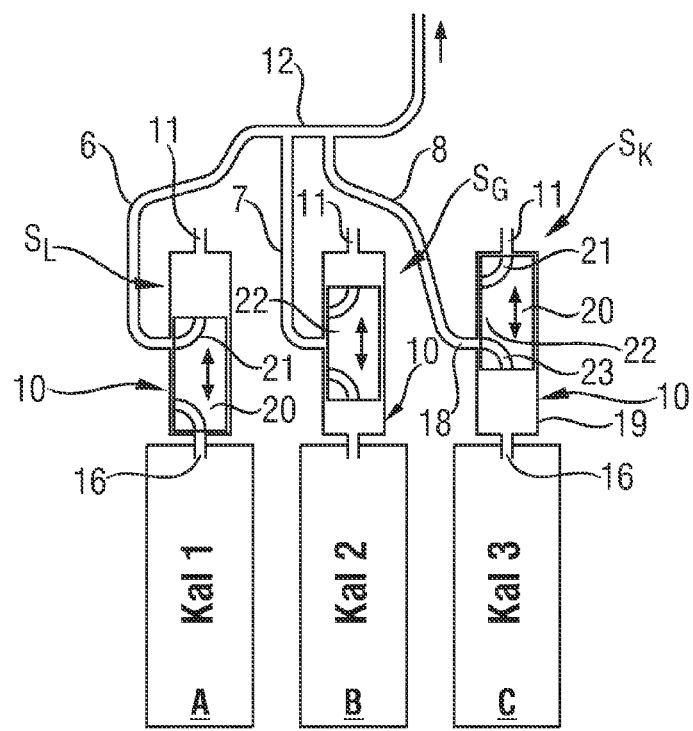
FIG. 2 is a diagram showing an embodiment of a first variant of a detail of a reagent cartridge according to the invention with the bag valves realized as piston valves and a common rail.

In the variant shown in FIG. 2 each multi-way valve 10 (bag valve) is realized as a piston valve, having a first fitting 16, which is heat-sealed or glued into a peripheral seam 17 (see FIG. 4) of the reagent bag A, B and C. Furthermore, each piston valve 10 has a hose fitting 18 for a connecting line 6, 7, 8. In the valve housing 19 of the piston valves a valve piston 20 can be axially shifted, which has a sealing region 22 between a first 21 and a second 23 transfer passage, each of which passages/regions 21, 22, 23 may be aligned with the fitting 18 by shifting the valve piston 20. In the first valve position SK the reagent can be sucked from the bag C via the transfer passage 23. In the second valve position SL the bag A is closed and air is sucked in via the transfer passage 21 in the piston 20 and the fluid path 11. In position SG the bag fitting 16 as well as the fluid path 11 are closed by the sealing region 22. For a concrete variant the individual valve positions are shown in detail in FIGS. 6 to 8.

Figure 3:
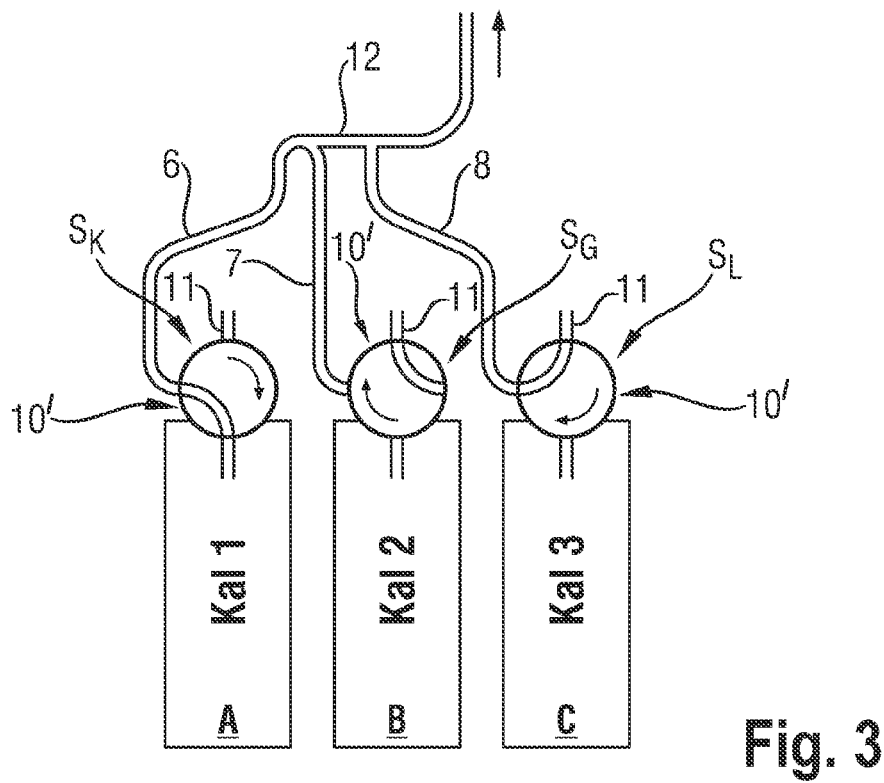
FIG. 3 is a diagram showing an embodiment of a second variant of a detail of a reagent cartridge according to the invention with the bag valves realized as rotary valves and a common rail.

The embodiment of FIG. 3 shows a variant of the invention, in which the multi-way valves are realized as rotary valves 10', which in a first rotational position SK establish a fluid path between the connecting lines 6, 7, 8 and the reagent bags A, B, C and in a second rotational position SL establish a fluid path 11 between a ventilation source, which in one embodiment is ambient air, and the connecting lines 6, 7, 8. Here also the connecting lines 6, 7, 8 open directly and without valves into the common rail 12 and may be sucked dry and free of fluid over their entire length, contamination of the bag content being avoided. In position SG the bag fitting 16 as well as the fluid path 11 are closed by the rotary valve 10'.

Figure 4:
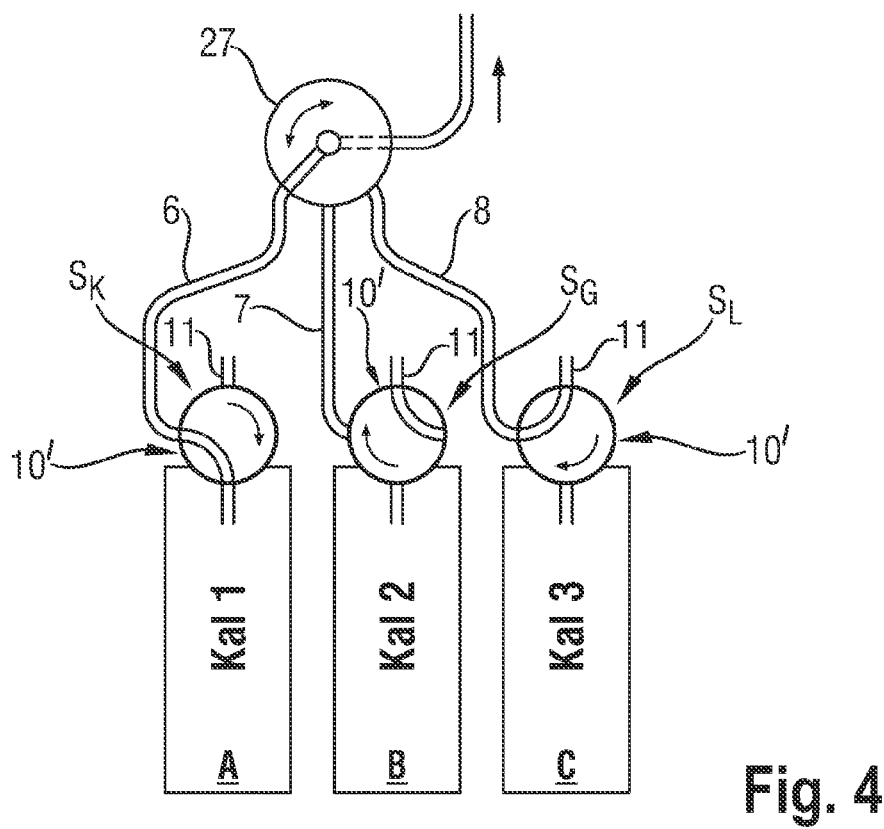
FIG. 4 is a diagram showing an embodiment of a third variant of a detail of a reagent cartridge according to the invention with the bag valves realized as rotary valves and a common collector valve.

In the variant of FIG. 4 the connecting lines 6, 7, 8 of the reagent bags A, B, C departing from the multi-way valves 10' lead directly to a collector valve 27 preceding the sample input device, which in one embodiment is a rotary valve. In this variant too, all fluid paths can be sucked dry and free of fluid, while contamination of the bag content is avoided.

As shown in FIG. 5 the coupling between the reagent bags A to D and the first fitting 16 is realized as a butterfly connection into which a piston valve 10 is integrated. The butterfly connections may in one embodiment be glued or in another embodiment heat-sealed into a peripheral or lateral seam 17 of the bags.

A reagent bag A, B, C, D according to the invention with a valve 10 located at the beginning of one of the connecting lines 6, 7, 8, 9, which has a first valve position (open position) and a second valve position (closed position), is thus characterized by the fact that in the closed position a fluid path 11 is opened between a ventilation source, which in one embodiment is ambient air, and a connecting line 6, 7, 8, 9 (see FIG. 8). The valve piston 20 is provided with an orifice 24 into which an actuating element 25 of the analyzer locks, which element is moved up and down—as indicated by arrows—to switch from one valve position to the other.

Referring to the piston valve 10 (see FIGS. 6 to 8) the three different positions of the valve are shown in an exemplary way:

FIG. 6, Valve position SK: functional fluid is sucked from the bag via the first fitting 16 (bag connection), transfer passage 23 (for instance a groove or planed area in the valve piston 20), and the second fitting 18 (tube connection);

FIG. 7, Valve position SG: the bag valve is closed (closed position);

FIG. 8, Valve position SL: ambient air is sucked in via transfer passage 21 (e.g., an annular gap) and/or a channel in the valve housing, while the bag fitting 16 is closed off.

The sealing region 22 of the valve piston 20 can be separated from each of the adjacent transfer passages 21, 23 by an O-ring seal 26.

When a new reagent cartridge 2 is inserted into the analyzer 1 and when the cartridge is in its delivery state all bag valves 10 are in position SG (see FIG. 7). The connection lines 6 to 9 are free of fluid.

Following will be some examples of the use of the reagent cartridge of the invention.

Example 1

Generating a Fluid Packet from Reagent Bag A for Measuring in the Measuring Chamber The procedure shown in table 1 (provided below) starts from an initial state (step 1), in which the fluid lines from the respective bag valve 10 to the measuring chamber 5 are filled with air. All bag valves 10 are in position SG, the hose pump 29 is deactivated and the input unit 13 is in the docking element 14 (posW).

The packet size, i.e., the amount or volume of fluid from reagent bag A, may be determined by timing or by the signal of monitoring sensors deployed in the line to the measuring chamber 5.

Optional steps preceding step 1 for initialising the application of the example, which are not further described here, may be provided. For terminating the application of the example, optional steps following steps 1 to 8 are possible (again not further described).

TABLE 1

| Step | Valve position bag A | Valve position bags B-D | Position of Input unit 13 | Action |
|---|---|---|---|---|
| 1 | SG | SG | PosW | Standby |
| 2 | SG->SK | SG | PosW | Valve at A in position SK |
| 3 | SK | SG | PosW | By means of the pump fluid is sucked from bag A via common rail 12 and docking element 14 into or through the measuring chamber 5. |

TABLE 1-continued

| Step | Valve position bag A | Valve position bags B-D | Position of Input unit 13 | Action |
|---|---|---|---|---|
| 4 | SK->SL | SG | PosW | Valve at A in position SL |
| 5 | SL | SG | PosW | By means of the pump air is sucked in from valve fitting 11 until the tube system up to the measuring chamber 5 is filled with air. |
| 6 | SL | SG | PosW | The pump for fluid transport is stopped and the fluid can be measured in the measuring chamber 5. |
| 7 | SL->SG | SG | posW | Valve at A in position SG |
| 8 | SG | SG | posW | Continue at step 1 |

Example 2

Rinsing and Preparing for Positioning a Sample in the Measuring Chamber

In one embodiment the multi-way valve of at least one reagent bag containing rinsing, flushing or disinfectant fluid, is alternatingly switched from a first valve position (SK) for sucking in fluid to a second valve position (SL) for sucking in a gaseous medium, such as for example air, thus alternatingly forming fluid and gas packets, which are transported through the line system of the analyzer into the measuring chamber. It has been found that cleaning the measuring chamber by alternatingly flushing it with fluid packets and separating air packets is of particular advantage.

The procedure shown in table 2 starts from an initial state (step 1), in which the connecting lines from the respective bag valve 10 to the measuring chamber 5 are air-filled. All bag valves 10 are in position SG, the pump 29 is deactivated and the input unit 13 is in the docking element 14 (posW).

TABLE 2

| Step | Valve position bag A | Valve position bag B | Valve position bag C-D | Action |
|---|---|---|---|---|
| 1 | SG | SG | SG | Standby |
| 2 | SG→SK | SG | SG | Valve at A in position SK |
| 3 | SK | SG | SG | By means of the pump fluid from bag A is sucked into the measuring chamber 5 via common rail 12 and docking element 14. |
| 4 | SK→SG | SG→SL | SG | While the pump is still working the valves A and B are actuated synchronously. Transport of fluid from bag A is interrupted and air is sucked in at valve B. This generates a separating air packet in the common rail 12. |
| 5 | SG→SK | SL→SG | SG | While the pump is still working valves A and B are actuated synchronously. Sucking in of air at the valve of bag B is ended and fluid is again sucked in from bag A. |
| 6 | SK | SG | SG | To generate more separating air packets go to step 4, otherwise continue at step 7. |
| 7 | SK→SL | SG | SG | By means of the pump air is sucked in at the fluid fitting 11, filling the tube system up to the measuring chamber 5 with air. |
| 8 | SL→SG | SG | SG | The pump is deactivated and the bag valves 10 are brought to their initial position. |
| 9 | SG | SG | SG | Continue at step 1 |

By repeating steps 4-5 any number of fluid packets and separating gas packets (e.g. air packets) necessary for cleaning the apparatus may be generated.

Example 3

Partially Filling the Connecting Lines 6 to 9 of Reagent Bags A to D with Fluid

In the embodiment with a common rail 12 (see FIG. 1 to FIG. 3) it has been found that in the case where fluid, in particular a calibrating fluid containing dissolved gases, is sucked through a connecting line 6 and the common rail 12, contact is established between the flowing fluid and the gas present in the other connecting lines 7, 8, 9, resulting in a concentration change of the gases dissolved in the fluids. This is a disadvantage when calibrating fluids for gas sensors are concerned.

During transport of fluid and separating gas packets in one embodiment pressure in the gas-containing connecting lines of the reagent bags is first lowered, which in one embodiment by a short-term increase of the rpm of the hose pump 29 provided in the analyzer for fluid transport, and thereafter pressure is raised again, which in one embodiment by reducing the rpm of the hose pump 29, thus bringing it back to normal operating speed, such that fluid is introduced into parts of the connecting lines 6, 7, 8, 9 opening into a common rail 12.

Thus a procedure has been designed for filling the connecting lines 7 to 9 partly with fluid next to the point where they open into the common rail 12. This is based on a short-term increase of the suction rate of pump 29 and the negative pressure thus generated in the connecting lines 7 to 9. When the suction rate of pump 29 is returned to its normal value, the gas volumes in the connecting lines 7 to 9 contract and the connecting lines are partially filled with fluid from the common rail 12.

The procedure shown in table 3 again starts from an initial state (step 1), which has been described in example 1.

TABLE 3

| Step | Valve position bag A | Valve position bag B | Valve position bag C-D | Action |
|---|---|---|---|---|
| 1 | SG | SG | SG | Standby |
| 2 | SG→SK | SG | SG | Valve at A in position SK |
| 3 | SK | SG | SG | By means of pump 29 fluid from bag A is sucked to the measuring chamber 5 via connecting line 12 and docking element 14. |
| 4 | SK | SG | SG | The suction rate of pump 29 is increased for a short time, such that fluid A is transported at a higher rate. Simultaneously negative pressure develops in the entire tube system, causing gas volumes in the connecting lines 7 to 9 to expand. This in turn causes a small amount of gas to move from the connecting lines 7 to 9 into the common rail 12. |
| 5 | SK | SG | SG | The suction rate is again lowered to its normal value. The concomitant decay of negative pressure in the entire tube system causes gas volumes to contract in the connecting lines 7 to 9. This causes the connecting lines 7 to 9 to be partially filled with fluid A via the common rail 12. |
| 6 | SK | SG | SG | Fluid A continues to be sucked in until the measuring chamber 5 is completely filled. |
| 7 | SK | SG | SG | Pump 29 stops and fluid A is measured in the measuring chamber. |
| 8 | SK→SL | SG | SG | Connecting line 6 of bag A is emptied via common rail 12 and measuring chamber 5 by means of pump 29. |
| 9 | SL→SG | SG→SL | SG | Connecting line 7 of bag B is emptied via common rail 12 and measuring chamber 5 by means of pump 29. |
| 10-n | SG | SL→SG | SG→SL | Connecting lines 8, 9, . . . of bags C, D, . . . are emptied via common rail 12 and measuring chamber 5 by means of pump 29. |
| 11 | SG | SG | SL→SG | All valves are closed. |
| 12 | SG | SG | SG | Standby |

Example 4

Use of a Collector Valve (Multi-Way Valve) Instead of a Common Rail

The procedure shown in table 4 gives an example of the use of a collector valve, e.g. a rotary valve 27, instead of a common rail 12. The rotary valve 27 for instance has positions 27-6, 27-7, 27-8 (connecting respectively to connecting line 6, 7 and 8 as shown in FIG. 4).

In this case no closed position SG of the bag valves is required, i.e., two valve positions of the bag valves are sufficient.

TABLE 4

| Step | Valve position at bag A | Valve position at bag B | Valve position collector valve 27 | Action |
|---|---|---|---|---|
| 1 | SL | SL | 27-6 | Standby |
| 2 | SL->SK | SL | 27-6 | Valve at A in position SK |
| 3 | SK | SL | 27-6 | By means of the pump fluid from bag A is sucked into and through the measuring chamber 5 via collector valve 27 and docking element 14. |

TABLE 4-continued

| Step | Valve position at bag A | Valve position at bag B | Valve position collector valve 27 | Action |
|---|---|---|---|---|
| 4 | SK->SL | SL | 27-6 | Valve at A in position SL |
| 5 | SL | SL | 27-6 | By means of the pump air is sucked in at valve opening 11, filling the tube system up to the measuring chamber 5 with air. |
| 6 | SL | SL | 27-6 | The fluid transport pump is stopped and the fluid can be measured in the measuring chamber 5. |
| 7 | SL | SL | 27-6 | Continue at step 1 |

Persons skilled in the art will appreciate that the embodiments described herein may be subject to various improvements and/or modifications that may be apparent without departing from the spirit and scope of these embodiments.

What is claimed is:

1. A reagent cartridge, which is exchangeably insertable into an analyzer having an input device and a ventilation source, said reagent cartridge comprising a plurality of flexible reagent bags, each of said reagent bags having a peripheral seam and being furnished with an analyzer-controlled multi-way valve, said multi-way valve comprises a valve housing which is connected directly to and extends within the reagent bag, wherein a connecting line departs directly from said valve housing which is connectable to the input device of the analyzer, wherein each analyzer-controlled multi-way valve has at least two valve positions, wherein a first valve position opens a fluid path between the connecting line and the reagent bag, and a second valve position closes off the reagent bag and opens a fluid path between the ventilation source and the connecting line, wherein the multi-way valve is heat-sealed or glued into the peripheral seam of the reagent bag.

2. The reagent cartridge according to claim 1, wherein the connecting lines of the reagent bags departing from the multi-way valves open directly into a common rail preceding the input device.

3. The reagent cartridge according to claim 1, wherein the connecting lines of the reagent bags departing from the multi-way valves open directly into a collector valve preceding the input device.

4. The reagent cartridge according to claim 3, wherein said collector valve is a rotary valve.

5. The reagent cartridge according to claim 1, wherein each multi-way valve of the reagent bags has a third valve position, in which access to the reagent bags as well as the fluid path to the ventilation source is closed.

6. The reagent cartridge according to claim 1, wherein each multi-way valve of the reagent bags is configured as a piston valve, which has a first fitting provided in a peripheral seam of the reagent bag and a second fitting joined to one of said connecting lines, and wherein a valve piston slides axially in a valve cylinder of the piston valve, said piston having a sealing region between a first and a second transfer passage, where by shifting the valve piston each passage or region is individually aligned with the second fitting.

7. The reagent cartridge according to claim 1, wherein each multi-way valve of the reagent bags is configured as a rotary valve, which in a first rotary position establishes a fluid path between one of said connecting lines and the reagent bag, and in a second rotary position establishes a fluid path between a ventilation source.

8. The reagent cartridge according to claim 1, wherein the ventilation source is ambient air.

9. The reagent cartridge according to claim 6, wherein the first fitting is glued into a peripheral seam of the reagent bag.

10. The reagent cartridge according to claim 6, wherein the first fitting is heat-sealed into a peripheral seam of the reagent bag.

11. A flexible reagent bag having a peripheral seam and including an analyzer-controlled multi-way valve that comprises a valve housing which is directly connected to and extends within the reagent bag, wherein a connecting line departs directly from said valve housing which is connectable to an input device of an analyzer, said valve having a first valve position which opens a first fluid path between the flexible reagent bag and the connecting line, thereby allowing a liquid within the reagent bag to be supplied to the connecting line, and a second valve position which closes off the reagent bag and opens a second fluid path between a ventilation source and the connecting line, wherein the multi-way valve is heat-sealed or glued into the peripheral seam of the reagent bag.

12. The reagent bag according to claim 11, wherein the valve has a third valve position, in which both the first and second fluid paths are closed.

* * * * *